United States Patent [19]

Pouchol et al.

[11] Patent Number: 5,834,448
[45] Date of Patent: Nov. 10, 1998

[54] DOSAGE FORM OF HYDROXOCOBALAMIN AND ITS USE IN CYANIDE POISONING

[75] Inventors: Gerard Pouchol, Paris; Yves Bonhomme, Charbonnieres; Marie-Laure Poulain, St-Cyr-En-Val; Michel Duran, St-Cyr-Au-Mont-d'or, all of France

[73] Assignee: Merck Patent Gesellschaft mit beschrankter Haftung, Germany

[21] Appl. No.: 748,790

[22] Filed: Nov. 14, 1996

[30] Foreign Application Priority Data

Nov. 15, 1995 [FR] France .................................. 95 13512

[51] Int. Cl.⁶ .................................................. A01N 57/00
[52] U.S. Cl. ........................................................ 514/81
[58] Field of Search .................................... 514/81

[56] References Cited

PUBLICATIONS

CA:72:103759 JP 45002758 Jan. 29, 1970.

*Primary Examiner*—Paul J. Killos
*Attorney, Agent, or Firm*—Millen, White, Zelano & Branigan, P.C.

[57] ABSTRACT

The invention relates to a new dosage form of hydroxocobalamin which serves in the treatment of cyanide poisoning and contains hydroxocobalamin in freeze-dried form. The hydroxocobalamin is freeze-dried in an acidic medium so as to be practically instantly redissolved in a neutral saline solution. The present invention also relates to a process for producing hydroxocobalamin-based pharmaceutical compositions as well as to first aid kits containing these compositions and methods of using such kits for the treatment of cyanide poisoning.

17 Claims, No Drawings

DOSAGE FORM OF HYDROXOCOBALAMIN AND ITS USE IN CYANIDE POISONING

BACKGROUND OF THE INVENTION

The present invention relates to the pharmaceutical field, and more particularly to that of therapeutic chemistry.

The subject of the present invention is more particularly a new dosage form of hydroxocobalamin which serves in the treatment of cyanide poisoning.

Agents for combating the lethal effects of cyanide poisoning are already known.

Kélocyanor®, which is provided in the form of an injectable solution, is a dicobalt salt of edetic, acid. The dicobalt salt of edetic acid is ionized into cobalt edetate$^-$ and into cobalt$^{++}$; the cobalt $^{++}$ ion combines with two cyanide$^-$ ions; the dicobalt salt: further ionizes slowly to produce another cobalt$^{++}$ ion which generally combines with two cyanide$^-$ ions. The cyanide-cobalt complexes are very stable and are removed in the urine.

The disadvantage of this medicinal product is that cobalt is present on its own, in ionized form,, which exhibits a high degree of toxicity and causes a multitude of undesirable effects.

It has already been proposed to use solutions of hydroxocobalamin to combat the poisoning caused by hydrocyanic acid and to diagnose chronic hypercyanogenesis (French Patent No. 2,153,156).

In this previous patent, use was made of fully ready hydroxocobalamin compositions combined with sodium thiosulphate. These compositions were intended for acute treatment by intravenous administration and for chronic treatment by intramuscular administration.

The dosage which is described therein provides, for the possibility of administering very high doses of hydroxocobalamin which may be as high as 30,000 $\mu$g. These anti-cyanide kits therefore required considerable doses of hydroxocobalamin. Furthermore, the combination with sodium thiosulphate conferred insufficient stability on the whole unit, the sodium thiosulphate being in particular a reducing and alkaline substance.

The combination of hydroxocobalamin with $Na_2S_2O_3$ for the treatment of cyanide poisoning ("Chemical Abstracts", Vol. 64, 1966, column 14, 849, a–d) is also known.

SUMMARY OF THE INVENTION

The present invention makes it possible to overcome these stability defects by providing a new therapeutic composition having hydroxocobalamin in freeze-dried form which can be redissolved at the time of use in a saline, preferably physiological saline, solution.

Physiological saline solution has the advantage of being stable because it does not become oxidized and does not become reduced, of being neutral because it is not alkaline; furthermore, it allows a practically instant dissolution of the freeze-dried product.

These characteristics are important because the hydroxocobalamin stability range is relatively narrow: solutions, reducing solutions and oxidizing solutions degrade hydroxocobalamin and cause it to lose its properties.

The freeze-dried form has numerous advantages; it allows indefinite preservation as well as a practically instant redissolution, provided this is performed in a slightly acidic medium.

Hydroxocobalamine naturally has an alkaline pH, but the stability of hydroxocobalamin is better at acidic pH.

The bibliographic information as well as the monographs "hydroxocobalamin injection" of the various pharmacopoeias show that hydroxocobalamin solutions should be stabilized especially by the addition of protective substances (amino acids).

In all cases, the pH is set at values of between 3.5 and 5, whereas hydroxocobalamin base solution has a pH close to 9.

The present invention is therefore characterized by the fact that a stable freeze-dried hydroxocobalamin product is obtained by carrying out the freeze-drying starting with an aqueous solution which is slightly acidic, preferably between 3.5 and 5.5. The optimum pH zone ranges from 4.0 to 5.0.

The acidic pH is obtained by adding to the hydroxocobalamin solution a strong inorganic acid or an organic acid, such as for example hydrochloric acid, sulphuric acid or acetic acid, in a calculated amount.

It was necessary to check that the acidification of the solution of hydroxocobalamin base with hydrochloric acid did not block the active site of the molecule and that the latter conserved its $OH^- \rightleftharpoons CN^-$ exchanging power.

Cyanidation tests were carried out and they showed that all the cyanide ions introduced were attached.

For the freeze-drying needs, it may be advantageous to add to the aqueous solution a neutral inert substance such as for example arginine hydrochloride, lactose, glycine or sodium acetate.

A buffering agent, such as for example a sodium salt of an organic acid, may also be added to the aqueous hydroxocobalamin solution.

According to a preferred embodiment of the invention, the solution to be freeze-dried contains only hydrochloric acid, and in this manner, the freeze-drying pellet is perfectly homogeneous.

Freeze-drying in an acidic medium avoids degradation and gives in the end a purer and more stable product.

The concentration of hydroxocobalamin in the solution to be freeze-dried ranges from 1.0 to 5.0 g and preferably between 2.0 and 3.0 g per 100 ml.

The invention also comprises a process for producing hydroxocobalamin-based pharmaceutical compositions which consists in preparing a hydroxocobalamin solution in water, in adjusting the pH to a value ranging from 3.0 to 5.0 by the controlled addition of an inorganic or organic acid and, where appropriate, of a filler and/or of a buffering agent, and then in carrying out the freeze-drying, in preparing, moreover, ampoules of saline solution with a volume of between 20 and 150 ml. The saline solution used for the redissolution is preferably a solution of sodium chloride and in particular a solution isotonic to plasma at 9 p. thousand in purified water.

The subject of the invention is also the first aid kit for the treatment of cyanide poisoning, consisting, on the one hand, of the vial of freeze-dried product containing between 1.0 and 5.0 g of hydroxocobalamin and an ampoule containing from 20 to 150 ml of a saline solution allowing the redissolution of hydroxocobalamin.

These kits exhibit perfect stability and can therefore be stored in medicine cabinets for a long period.

The subject of the invention is also the use of the hydroxocobalamin-based kits for the treatment of acute or chronic cyanide poisoning, which consists in administering, via the intravenous route, the reconstituted contents of the aqueous hydroxocobalamin solution.

EXAMPLE 1

Unit Composition

1) Formulas of the hydroxocobalamin solutions with adjustment of the pH

| | | |
|---|---|---|
| a) | Hydroxocobalamine base | 0.250 g |
| | Sodium acetate | 0.540 g buffer |
| | | pH = 4.6 |
| | Acetic acid | 0.240 g |
| | Water for injection qs | 10.000 ml |
| b) | Hydroxocobalamine base | 0.250 g |
| | Sodium acetate | 0.188 g |
| | Sodium chloride | 0.041 g |
| | Acetic acid | 0.041 g |
| | Water for injection qs | 10.000 ml |
| c) | Hydroxocobalamine base | 0.250 g |
| | HCl 0.1N qs | pH = 4.0 |
| | Water for injection qs | 10.000 ml |
| d) | Hydroxocobalamine base | 0.250 g |
| | HCl 0.1N qs | pH = 5.0 |
| | Water for injection qs | 10.000 mL |
| e) | Hydroxocobalamine base | 0.250 g |
| | Sodium acetate | 0.166 g |
| | Sodium chloride | 0.041 g |
| | Acetic acid qs | pH = 4.0 |
| | Water for injection qs | 10.000 ml |

2) Formulas for the hydroxocobalamin solutions with protective substances

| | | |
|---|---|---|
| f) | Hydroxocobalamine base | 0.250 g |
| | Arginine hydrochloride | 0.010 g |
| | Water for injection qs | 10.000 ml |
| g) | Hydroxocobalamine base | 0.250 g |
| | Lactose | 0.033 g |
| | Water for injection qs | 10.000 ml |
| h) | Hydroxocobalamine base | 0.250 g |
| | Glycine | 0.033 g |
| | Water for injection qs | 10.000 ml |

Solutions f), g) and h) were divided into 2 and each half was acidified.

| | |
|---|---|
| Hydroxocobalamine base | 2.5 g |
| HCl 0.1N qs | pH = 4.0 |
| Water for injection qs | 100.0 ml |

EXAMPLE 2

Solubility of the Freeze-Dried Product in Physiological Saline

1) Procedure

Add to a vial of freeze-dried product (about 2.5 g) 125 ml of physiological saline.

Shake the vial vigorously for exactly 30 seconds.

Filter the solution immediately on a cellulose acetate membrane with a porosity of 0.45 μm and a diameter of 47 mm (SARTORIUS ref. 11106).

After draining the membrane (bottom face placed on absorbent filter paper), examine the particles which may be present therein under a microscope. Also examine the walls of the vial to check that the solubility was complete.

Then introduce the filter with the collected particles into a beaker containing 25.0 ml of mobile phase used for HPLC analysis.

Soak the filter rapidly and stir it in order to detach or solubilize the particles which may be present. Inject the solution obtained for HPLC.

2) Tests carried out

Two tests were carried out on:

1 vial of freeze-dried product +125 ml of physiological saline stored at laboratory temperature (21° C.)

1 vial of freeze-dried product +125 ml of physiological saline stored in a refrigerator before use (+5° C.)

3) Results

Visual examination of the empty vials makes it possible to observe that no undissolved particle remains on the walls of the vial for the 2 temperature conditions tested.

Microscope examination of the membrane makes it possible to visualize a few small colourless crystals and 1 or 2 pink-coloured crystals. The result is similar under the two temperature conditions.

HPLC analysis of the solutions which served to soak the filters (with the possible residue collected) indicates that the quantity of hydroxocobalamin found could represent at most 0.03% of the quantity present in the vials. The result is similar for the two storage conditions tested.. This percentage in fact covers the solubilized hydroxocobalamin brought by the solution which impregnates the filter and possibly nonsolubilized hydroxocobalamin.

EXAMPLE 3

Stability of the Solution After Reconstitution During The Duration of Perfusion 1) Operating conditions a) Preparation of the solutions Test with exposure to ambient laboratory temperature and light Open a vial of freeze-dried product containing 2.5 g of hydroxocobalamin.

Add 125 ml of a solution of sodium chloride at 9 p. thousand in purified water.

Shake manually and vigorously for 30 s.

Using a graduated pipette, introduce 5.0 ml of the solution obtained into a 100 ml graduated flask. Bring to the required volume with the mobile phase used for the chromatography. Inject this solution immediately for HPLC (analysis at time T0).

Keep the vial containing the reconstituted solution in daylight and at room temperature (20° to 22° C.) on a shelf in front of a laboratory window. The laboratory is also illuminated by neon-type lamps.

After storing the reconstituted solution for 2 h, 4 h, 6 h and 8 h under the above conditions, collect samples from the vial and analyse the sample by HPLC immediately as indicated for the initial analysis at time T0.

Test with exposure under a UV lamp at 366 nm

Carry out the procedure as indicated in the test with the exposure at ambient laboratory temperature and light, the reconstituted solution being stored under a UV lamp at 366 nm.

Collect a sample at time T0 and after storing for 1 h, 3 h and 5 h under UV at 366 nm.

b) Chromatographic analyses

The area of the intact hydroxocobalamin peak and the content of related substances in the solutions reconstituted at time 0 and after storage are determined by HPLC.

2) Results

The detailed results of the HPLC analyses carried out on the samples collected after various storage times of the hydroxocobalamin solutions obtained after reconstitution of a vial of freeze-dried product (about 2.5 g of hydroxocobalamin base with 125 ml of NaCl solution at 9 p. thousand) are presented:

in Table 1: for the reconstituted solution stored under conditions of ambient laboratory temperature and light, in Table 2: for the reconstituted solution under UV lamp at 366 nm.

The absolute value of the contents of related substances measured in the reconstituted solution is not completely exact. It is calculated for an exact final volume of 125 ml. It is however comparable over the entire period of storage of the same solution.

To assess the stability of the hydroxocobalamin solutions, the following should be considered in particular:

the variation of the hydroxocobalamin peak area measured at each storage time compared with the hydroxocobalamin peak area measured on the same solution at time T0;

the variation of the contents of related substances measured during storage compared with the contents of related substances measured at time T0 on the same solution.

Variation of the content of intact hydroxocobalamin found during storage:

After storing the reconstituted solution for 8 hours under conditions of ambient laboratory light and temperature and after storing for 5 hours under UV lamp at 366 nm, no significant decrease is observed in the hydroxocobalamin peak area compared with the analyses carried out at time T0 on the reconstituted solutions.

If there is a decrease in the hydroxocobalamin, content, this decrease is low and insufficient to be detected by HPLC given the precision of the analytical method.

Variation of the contents of substances related to hydroxocobalamin during storage:

The increase in the contents of substances related to hydroxocobalamin detected by HPLC, after storing for 8 hours under conditions of ambient laboratory temperature and light and after storing for 5 hours under UV lamp at 366 nm remains very limited: about 1 p. cent.

TABLE 1

ASSAY OF HYDROXOCOBALAMIN AND RELATED SUBSTANCES AFTER RECONSTITUTION
EXPOSURE TO DAYLIGHT

|  | RT | RRT | control 100% | T0 | T 2H | T 4H | T 6H | T 8H |
|---|---|---|---|---|---|---|---|---|
| AREAS | 9.108 | 0.45 | 57616 | 58786 | 59985 | 54130 | 58406 | 59531 |
|  | 10.883 | 0.54 | 66134 | 64167 | 69257 | 63020 | 68001 | 70589 |
|  | 11.882 | 0.59 | 23607 | 37327 | 49821 | 38212 | 46438 | 44820 |
|  | 13.735 | 0.68 | 20859 | 14089 | 20064 | 10884 | 16572 | 17123 |
|  | 16.388 | 0.82 | 16894 | 20932 | 29809 | 22837 | NI | 25952 |
|  | 17.725 | 0.88 | 179243 | 220728 | 224772 | 243506 | 299941 | 276644 |
|  | 20.052 | 1.00 | 18379040 | 18341948 | 18863300 | 17675508 | 18279040 | 18168326 |
|  | 26.043 | 1.30 | 29265 | 49659 | 30579 | 50000 | 61549 | 45724 |
|  | 38.49 | 1.92 | 9212 | 151908 | 215684 | 205421 | 194838 | 190731 |
|  | 53.145 | 2.65 |  |  | 26971 | 27447 | 22015 | 41413 |
|  | sum Ai |  | 402830 | 617596 | 726942 | 715456 | 767760 | 77252 |
|  | control batch 57917 |  | TW | 61.65 | mg | T % sec | 100.8 |  |
|  |  |  | c | 1.022 | mg/ml | H % | 17.8 |  |
|  | control 5% |  | A= | 930847 |  | T% as such | 82.8576 |  |
|  |  |  | AM (g) | 2.656 | 2.656 | 2.656 | 2.656 | 2.656 |
| % rela- ted sub- stan- ces | | 0.45 | 0.32 | 0.32 | 0.33 | 0.30 | 0.32 | 0.33 |
| | | 0.54 | 0.36 | 0.35 | 0.38 | 0.35 | 0.37 | 0.39 |
| | | 0.59 | 0.13 | 0.20 | 0.27 | 0.21 | 0.25 | 0.25 |
| | | 0.68 | 0.11 | 0.08 | 0.11 | 0.06 | 0.09 | 0.09 |
| | | 0.82 | 0.09 | 0.11 | 0.16 | 0.13 | * | 0.14 |
| | | 0.88 | 0.98 | 1.21 | 1.23 | 1.34 | 1.65 | 1.52 |
| | | 1.00 | | | | | | |
| | | 1.30 | 0.16 | 0.27 | 0.17 | 0.27 | 0.34 | 0.25 |
| | | 1.92 | 0.05 | 0.83 | 1.18 | 1.13 | 1.07 | 1.05 |
| | | 2.65 | 0.00 | 0.00 | 0.15 | 0.15 | 0.12 | 0.25 |
| related substances (%): | | | 2.21 | 3.39 | 3.99 | 3.93 | 4.21 | 4.24 |
| % hydroxocobalamin relative to T0 | | | | 100.0% | 102.8% | 96.4% | 99.7% | 99.1% |

NI: not integrated
*taken into account in the peak of RRT 0.88

TABLE 2

ASSAY OF HYDROXOCOBALAMIN AND RELATED SUBSTANCES AFTER RECONSTITUTION
EXPOSURE UNDER UV LAMP AT 366 nm

|  |  | RRT | control 100% | T0 | T 1H |  |  | T 3H | T 5H |
|---|---|---|---|---|---|---|---|---|---|
|  | RT |  |  |  |  |  |  |  |  |
| AREAS | 9.423 | 0.43 | 58375 | 61403 | 57524 |  |  | 59669 | 61494 |
|  | 11.38 | 0.52 | 62877 | 71503 | 66314 |  |  | 69342 | 69934 |
|  | 12.423 | 0.57 | 29963 | 47572 | 46343 |  |  | 42826 | 34806 |
|  | 14.49 | 0.67 | 24104 | 23374 | 18195 |  |  | 12293 | 9748 |
|  | 17.425 | 0.80 | 27503 | 27183 | 39478 |  |  | 38154 | 42460 |
|  | 18.797 | 0.87 | 172368 | 220359 | 207299 |  |  | 233187 | 275029 |
|  | 21.715 | 1.00 | 18203892 | 18167878 | 17683928 |  |  | 18236596 | 18135146 |
|  | 29.758 | 1.32 | 25323 | 28171 | 76643 |  |  | 32907 | 72284 |
|  | 43.808 | 2.02 | 7027 | 179220 | 212275 |  |  | 207668 | 212788 |
|  | 60.277 | 2.78 |  |  | 24889 |  |  | 36611 | 52788 |
|  | sum A1 |  | 407540 | 658785 | 748960 |  |  | 732657 | 831331 |
|  | control batch |  |  |  |  |  |  |  |  |
|  | 57917 | TW | 61.65 | mg | T | %sec | | 100.8 |  |
|  | control 5% | c | 1.022 | mg/ml | H | % | | 17.8 |  |
|  |  | S≈ | 951271 |  | T | % as such | | 82.8576 |  |
|  |  | AM (g) |  | 2.656 | 2.656 |  |  | 2.656 | 2.656 |
| % |  | 0.43 | 0.31 | 0.33 | 0.31 |  |  | 0.32 | 0.33 |
| rela- |  | 0.52 | 0.34 | 0.38 | 0.36 |  |  | 0.37 | 0.38 |
| ted |  | 0.57 | 0.16 | 0.26 | 0.25 |  |  | 0.23 | 0.19 |
| sub- |  | 0.67 | 0.13 | 0.13 | 0.10 |  |  | 0.07 | 0.05 |
| stan- |  | 0.80 | 0.15 | 0.15 | 0.21 |  |  | 0.20 | 0.23 |
| ces |  | 0.87 | 0.93 | 1.18 | 1.11 |  |  | 1.25 | 1.48 |
|  |  | 1.00 |  |  |  |  |  |  |  |
|  |  | 1.32 | 0.14 | 0.15 | 0.41 |  |  | 0.18 | 0.39 |
|  |  | 2.02 | 0.04 | 0.96 | 1.14 |  |  | 1.12 | 1.14 |
|  |  | 2.78 | 0.00 | 0.00 | 0.13 |  |  | 0.20 | 0.28 |
| related substances (%): |  |  | 2.19 | 3.54 | 4.02 |  |  | 3.93 | 4.46 |
| % hydroxocobalamin relative to T0 |  |  |  | 100.0% | 97.3% |  |  | 100.4% | 99.8% |

3) Conclusion

The results of this study show a satisfactory stability of the freeze-dried hydroxocobalamin product reconstituted with an aqueous solution of sodium chloride at 9 p. thousand in the proportions selected for administration of the product, over a period substantially covering the time necessary for the administration of a vial of freeze-dried product by slow perfusion.

The test of preservation performed under UV lamp at 366 nm appears to confirm that the light factor might not be a very critical parameter for the preservation of the hydroxocobalamin solutions for the period necessary for the administration of the product by perfusion.

The hydroxocobalamin compounds of this invention can be administered to treat cyanide poisoning analogously to Kélocyanor®.

The entire disclosures of all applications, patents and publications, cited above and below, and of corresponding application(s) French No. 95 13 512, filed Nov. 15, 1995, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising hydroxocobalamin in freeze-dried form, wherein the hydroxocobalamin is freeze-dried in an acidic medium so as to be rapidly redissolved in a neutral saline solution.

2. A pharmaceutical composition according to claim 1, wherein the freeze-dried hydroxocobalamin is redissolved in a saline solution.

3. A pharmaceutical composition comprising hydroxocobalamin in freeze-dried form according to claim 1, characterized in that the acidic medium within which the hydroxocobalamin is freeze-dried is selected so as to make it possible to obtain a stable solution.

4. A process for producing a freeze-dried hydroxocobalamin product according to claim 1, which comprises preparing the hydroxocobalamin solution in an acidic medium, optionally supplemented with a filler, and freeze-drying the hydroxocobalamin in the container intended to be used.

5. A process for producing a hydroxocobalamin product according to claim 1 which comprises preparing a hydroxocobalamin solution in an acidic medium, optionally supplemented with a filler, and freeze-drying the hydroxocobalamin, wherein said hydroxocobalamin solution has a pH ranging from 3.5 to 5.5.

6. A process for producing a freeze-dried hydroxocobalamin product according to claim 1 which comprises preparing a hydroxocobalamin solution in an acidic medium, optionally supplemented with a filler, and freeze-drying the hydroxocobalamin, wherein said hydroxocobalamin solution has a pH ranging from 4.0 to 5.0.

7. A process for producing a freeze-dried hydroxocobalamin product according to claim 1 which comprises preparing a hydroxocobalamin solution in an acidic medium, optionally supplemented with a filler, and freeze-drying the hydroxocobalamin, wherein the acidic pH is obtained by adding to a solution of hydroxocobalamin a strong inorganic acid or an organic acid in a calculated amount.

8. A process according to claim 5, wherein a filler chosen from arginine hydrochloride, lactose, glycine or sodium acetate is added to the hydroxocobalamin solution.

9. A process according to claim 5, wherein a buffering agent consisting of a sodium salt of an organic acid is added to the hydroxocobalamin solution.

10. A process according to claim 5, wherein the concentration of hydroxocobalamin in the solution to be freeze-dried ranges from 1 to 5 g per 100 ml.

11. A process according to claim 10, wherein the concentration of hydroxocobalamin in the solution to be freeze-dried is between 2 and 3 g per 100 ml.

12. A process for producing hydroxocobalamin-based pharmaceutical compositions which comprises preparing a solution of hydroxocobalamin in water, adjusting the pH to a value ranging from 3 to 5 by the controlled addition of an inorganic or organic acid and, where appropriate, a filler and/or a buffering agent, freeze-drying the hydroxocobalamin and preparing ampoules of saline solution having a volume of between 20 and 150 ml.

13. A process for producing hydroxocobalamin-based pharmaceutical compositions according to claim 12, in which the saline solution is a solution of sodium chloride.

14. A first aid kit for the treatment of cyanide poisoning consisting of a vial of freeze-dried hydroxocobalamin product, obtained according to the process of claim 5 containing between 1 and 5 g of hydroxocobalamin and an ampoule containing from 20 to 150 ml of a saline solution allowing redissolution of said freeze-dried hydroxocobalamin.

15. A method of using the hydroxocobalamin-based first aid kits according to claim 14, for the treatment of acute or chronic cyanide poisoning, which comprises intravenously administering the aqueous solution of redissolved hydroxocobalamin.

16. A pharmaceutical composition comprising hydroxocobalamin in freeze-dried form according to claim 1, characterized in that the acidic medium within which the hydroxocobalamin is freeze-dried is selected so as to make it possible to obtain a stable solution, with a hydroxocobalamin concentration in the range of 1 to 5 g per 100 ml.

17. A pharmaceutical composition consisting essentially of freeze-dried hydroxocobalamin redissolved in a saline solution.

* * * * *